United States Patent
Seibold

(10) Patent No.: US 7,988,215 B2
(45) Date of Patent: Aug. 2, 2011

(54) SURGICAL ROBOTIC SYSTEM

(75) Inventor: Ulrich Seibold, Burnaby (CA)

(73) Assignee: Deutsches Zentrum Fuer Luft-und Raumfahrt E.V. (DE)

( * ) Notice: Subject to any disclaimer, the term of this patent is extended or adjusted under 35 U.S.C. 154(b) by 555 days.

(21) Appl. No.: 12/151,251

(22) Filed: May 5, 2008

(65) Prior Publication Data

US 2008/0276746 A1 Nov. 13, 2008

(30) Foreign Application Priority Data

May 11, 2007 (DE) .......... 10 2007 022 122

(51) Int. Cl.
*B25J 15/02* (2006.01)
(52) U.S. Cl. .......... 294/88; 254/134.3 FT; 254/134.3 R; 606/205; 901/34
(58) Field of Classification Search .......... 294/88, 294/907; 254/134.3 FT, 134.3 R; 483/901; 606/205–208; 414/5, 6, 730, 739; 901/32, 901/33, 34, 41; 74/490.05
See application file for complete search history.

(56) References Cited

U.S. PATENT DOCUMENTS

| | | | |
|---|---|---|---|
| 4,456,293 A | 6/1984 | Panissidi | 294/106 |
| 4,995,148 A * | 2/1991 | Bonomi et al. | 29/26 A |
| 5,100,285 A * | 3/1992 | Wagner | 414/744.8 |
| 5,275,615 A | 1/1994 | Rose | 606/208 |
| 5,339,723 A * | 8/1994 | Huitema | 91/388 |
| 5,350,355 A * | 9/1994 | Sklar | 604/23 |
| 5,791,231 A * | 8/1998 | Cohn et al. | 92/88 |
| 5,871,250 A * | 2/1999 | Sawdon | 294/88 |
| 5,876,410 A * | 3/1999 | Petillo | 606/142 |
| 2003/0144671 A1* | 7/2003 | Brooks et al. | 606/108 |

FOREIGN PATENT DOCUMENTS

| | | |
|---|---|---|
| DE | 224 930 | 7/1985 |
| DE | 697 35 708 | 9/2006 |
| DE | 10 2005 046 160 | 3/2007 |

OTHER PUBLICATIONS

Examination Report for German Patent Application No. 10 2007 022 122 dated Feb. 5, 2008.
Examination Report for German Patent Application No. 10 2007 022 122 (with English translation) dated Feb. 5, 2008.

* cited by examiner

*Primary Examiner* — Saúl J Rodríguez
*Assistant Examiner* — Stephen Vu
(74) *Attorney, Agent, or Firm* — Ohlandt, Greely, Ruggiero & Perle, LLP

(57) ABSTRACT

A surgical robotic system includes a robotic arm, an end effector movably connected thereto and provided with a movable end effector element driven by an actuator, and a force sensor arranged between the robotic arm and the end effector. The actuator is formed by a hydraulic cylinder. The robotic arm is provided with a hydraulic line connected to said hydraulic cylinder of the end effector.

6 Claims, 1 Drawing Sheet

SURGICAL ROBOTIC SYSTEM

BACKGROUND

1. Field of the Disclosure

The present disclosure relates to a surgical robotic system comprising a robotic arm with an end effector attached thereon.

2. Discussion of the Background Art

In the field of minimal-invasive surgery, use is made of surgical robots as surgical instruments for performing e.g. gripping and cutting processes in the patient's body. For this purpose, a surgical robotic system comprises a robotic arm and, at the end of the robotic arm, an end effector including a movable end effector element. Said end effector element can be e.g. a forceps or a pair of scissors. On the end effector, an actuator is provided for moving the end effector element such as, e.g., an arm of a forceps.

Arranged between the end effector and the robotic arm is a force sensor for detection of the forces externally acting on the end effector, particularly of the gripping forces and the contact forces. Gripping forces are defined as the forces which are generated when the end effector is gripping an object which is not in contact with its environment. Contact forces are the forces generated by the contact between the end effector or a gripped object and the environment.

The force sensor arranged between the robotic arm and the end effector serves for detecting the forces generated by indirect or direct contact between the end effector and its environment. The gripping forces can be detected by detection of the closing and respectively gripping forces exerted by the actuator.

Surgical robotic systems of the minimal-invasive type are, at least in their invasive parts, considerably miniaturized under the mechanical aspect. In presently known surgical robotic systems, the actuators are realized as Bowden cables. The Bowden cables are occasionally required to transmit considerable pulling and pushing forces. Even in cases of a highly sophisticated construction, the driving forces transmitted by the Bowden cables will at least partially interfere with the contact forces. The reason for this effect resides, inter alia, in that the occurrence of axial pulling or pushing forces will inevitably cause a stretching or shortening of the sheath of the Bowden cable, with the unavoidable consequence that undesired driving forces are inserted into the end effector.

Due to manufacturing tolerances and due to the properties of the materials used in miniaturized mechanics, a friction- and loss-free transmission of forces, e.g. via Bowden cables, cannot be guaranteed anymore or can at best be guaranteed only with considerable difficulties. In larger gripping devices, by contrast, manufacturing tolerances and material properties do not cause a problem of the above kind; thus, larger gripping devices do allow for a substantially friction- and loss-free transmission of forces. Consequently, in larger gripping devices as used e.g. in industrial applications, the extent of mutual interference between driving forces transmitted by Bowden cables or other mechanical transmission devices will be lower or even negligible.

Further, concerning the mechanical transmission of the driving forces, production and assembly of the mechanics are getting increasingly difficult and complex because of the continuing progress in miniaturization.

In view of the above, it is an object of the present invention to provide a surgical robotic system wherein the detection of the contact force is improved.

SUMMARY

The surgical robotic system according to the disclosure comprises an end effector provided with a movable end effector element driven by an actuator. Between the robotic arm and the end effector, a force sensor is arranged. The actuator of the end effector is formed by a hydraulic cylinder used for driving the end effector element. The robotic arm is provided with a hydraulic line which is connected to the hydraulic cylinder.

Thus, the end effector is not driven by one or a plurality of Bowden cables but by hydraulic means. A hydraulic drive is virtually free of friction so that a force measurement by use of the force sensor will not be disturbed by the occurrence of frictional forces. The hydraulic line can be run within narrow radii or within decoupling loops. For instance, the free length of the hydraulic line between the robotic arm and the end effector can be made large enough to allow only negligibly small forces to be transmitted between the robotic arm and the end effector. The free length of the hydraulic line between the robotic arm and the end effector is preferably at least 2.0 mm. The free length of the hydraulic line is defined to be that length along which the hydraulic line between the robotic arm and the end effector is neither radially nor axially fixed.

During energy transmission for generating the gripping force by use of hydraulic liquid, the hydraulic line is subjected to forces in radial and axial directions alike. Of special interest here are the forces in the axial direction. Particularly, the cross section of the hydraulic line is considerably smaller than the effective cross section of the hydraulic cylinder. In this context, the forces generated in the axial direction are proportionate to the cross section and the effective pressure.

The hydraulic design of the actuator makes it possible, by very simple constructional means, to realize a very high reduction ratio from 1:10 to more than 1:100. Thus, very high reduction ratios can be obtained through a very simple, compact design of the end effector. In spite of the high forces which thus can be transmitted to the respective end effector element, the hydraulic pressure required for this purpose in the hydraulic line is relatively small. As a result, large pulling or pressure forces transmitted by the hydraulic cylinder to the end effector element will cause only small changes of length of the hydraulic line.

Preferably, the cross-sectional area of the hydraulic cylinder is at least ten times the cross-sectional area of the hydraulic line. The reduction ratio will thus amount to at least 1:10. Consequently, the axial forces in the shell of the hydraulic line will be no more than one tenth of the drive force transmitted by the hydraulic cylinder to the end effector element. The larger the reduction ratio is, i.e. the smaller the cross-sectional area of the hydraulic line is relative to the cross sectional area of the hydraulic cylinder, the better the mechanical decoupling will be.

Although a complete mechanical decoupling cannot be realized by means of a hydraulic drive either, the forces in relation to the cross sectional areas can be sufficiently decreased so that the drive forces—acting on the force sensor—which are provided to generate an actuator force acting on the end effector element, are reduced to the effect that the disturbing forces in comparison to the contact forces will be small and, apart from this, these forces can be computationally compensated for on the basis of the known mechanical interrelationships.

According to a preferred embodiment, the hydraulic cylinder is formed by a closed metallic bellows. The sealing means in hydraulic cylinders have to allow for smooth-running operation on the one hand and must offer absolute leak-tightness on the other hand. Under the effect of the sterilization process required in human medicine, such seals will be damaged over time so that their functional integrity cannot be guaranteed permanently. By contrast, a closed metallic bellows used as a hydraulic cylinder will not need any sealing means and will hermetically close the fluid space against the environment in a reliable manner.

Preferably, the hydraulic fluid is an isotonic sterile saline solution. Also in case of a leakage of the hydraulic cylinder or the hydraulic line, the patient would not be endangered by leaking hydraulic fluid.

According to a preferred embodiment, the hydraulic cylinder comprises two end effector elements which are symmetrically arranged and driven and are configured to form e.g. a forceps-like gripping means. Preferably, the hydraulic cylinder is mechanically coupled to the one or plural end effector elements in such a manner that, when the cylinder is being extended, i.e. when hydraulic fluid is pumped into the hydraulic cylinder, a closing or gripping movement is performed.

Preferably, the force sensor is designed as a force/moment sensor having up to six degrees of freedom.

Two embodiments of the disclosure will be explained in greater detail hereunder with reference to the accompanying drawings.

DETAILED DESCRIPTION OF PREFERRED EMBODIMENTS

Figure 1:
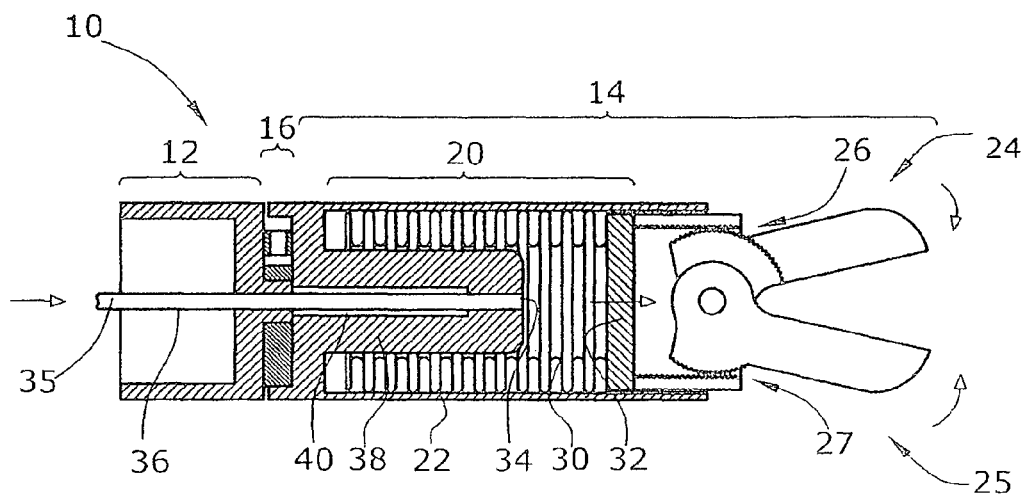
FIG. 1 is a view of a first embodiment of a surgical robotic system comprising two end effector elements, with the end effector elements arranged to perform a closing movement upon expansion of the hydraulic cylinder.
Figure 2:
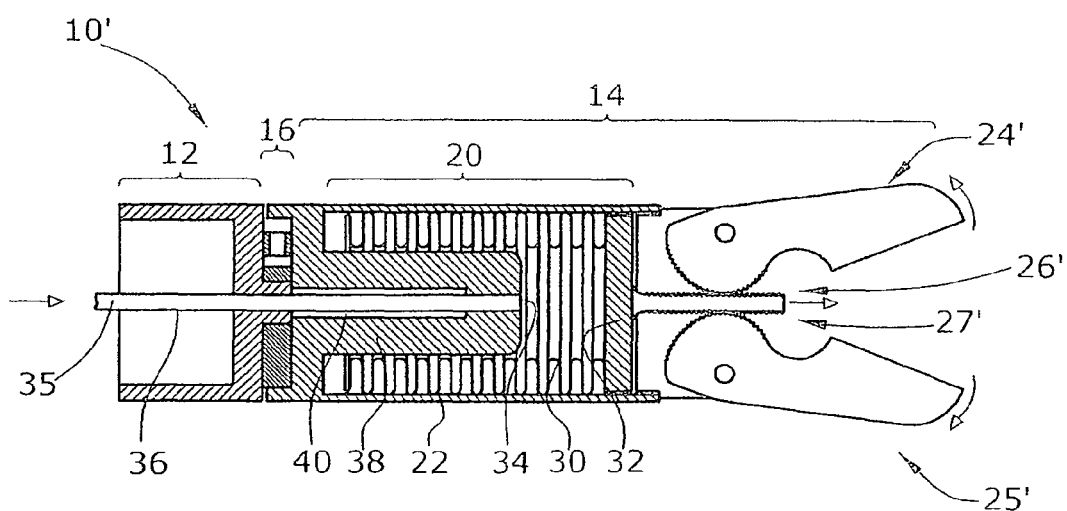
FIG. 2 is a view of a second embodiment of a surgical robotic system comprising two end effector elements, with the end effector elements arranged to perform an opening movement upon expansion of the hydraulic cylinder.

FIGS. 1 and 2 each illustrate a surgical robotic system 10 and respectively 10', said system forming a part of a surgical robot for use in minimal-invasive surgery. Each of the surgical robotic systems 10,10' shown in the Figures comprises a movable robotic arm 12 and an end effector 14 movably fastened to robotic arm 12. End effector 14 is fastened to robotic arm 12 via a force sensor 16 configured as a force/moment sensor with six arms.

End effector 14 comprises a hydraulic cylinder 20, a housing 22, two pivotable end effector elements 24,25 and toothed-rack drives 26,27; 26',27', each of the latter being assigned to a respective one of the end effector elements 24,25. The outer diameter of end effector 14 is 5 to 15 mm.

Hydraulic cylinder 20 is formed by a metallic bellows 30, a closure piston 32 and a hydraulic-line opening 34 of hydraulic line 36. Hydraulic line 36 has an internal cross-sectional area of about 0.2 mm$^2$. Said bellows 30 and respectively said hydraulic cylinder 20 have an effective cross-sectional area of about 19 mm$^2$.

Hydraulic line 36 is fixed on the distal end of said end effector 14 as well as on the distal end of a plunger 38 extending far into bellows 30. Between its fixation sites, plunger 38 is formed with a widened bore 40 along an axial length of about 5 mm, the inner diameter of bore 40 being larger than the outer diameter of hydraulic line 36. In this manner, hydraulic line 36 within end effector 14 has a free length of about 5 mm where said line is not fixed, neither axially nor radially.

As hydraulic fluid 35, use is made of an isotonic sterile saline solution. When hydraulic fluid 35 is pumped into hydraulic line 36 via a suitable pump which has been placed at an extracorporeal site, hydraulic cylinder 20 will expand correspondingly, thus moving the closure piston 32 in a distal direction. In the arrangement according to FIG. 1, this movement will cause the toothed-rack drives 26,27 to close the end effector elements 24,25 which are formed as forceps-like gripping means.

Force sensor 16 is substantially subjected to contact forces, said forces acting on the end effector 14 as a result of a contact of end effector 14 with its environment. Gripping forces can be detected with high accuracy by measurement of the hydraulic pressure.

In the embodiment of surgical robotic system 10' shown in FIG. 2, in contrast to the embodiment according to FIG. 1, the toothed-rack drive 26',27' is designed to function in the opposite manner so that an expansion of hydraulic cylinder 20 will cause the end effector element 24',25' to perform an opening movement.

For instance, at a drive pressure of 20 bar (allowable pressure of hydraulic cylinder 20), the force/moment sensor 16 is subjected to an axial force of Ah·P, with Ah representing the cross section of hydraulic line 36, and the tooth racks of gear 26,27 and respectively 26',27' are subjected to an axial force of Af·P, with Af representing the cross section of hydraulic cylinder 20. In this manner, the parasitic influence of the gripping drive force on the force/moment sensor 16 can be reduced substantially by a factor 100. The still remaining influence thereafter can be compensated for by computational means, provided that the drive pressure P is known at all times.

Although the disclosure has been described and illustrated with reference to specific illustrative embodiments thereof, it is not intended that the disclosure be limited to those illustrative embodiments. Those skilled in the art will recognize that variations and modifications can be made without departing from the true scope of the disclosure as defined by the claims that follow. It is therefore intended to include within the disclosure all such variations and modifications as fall within the scope of the appended claims and equivalents thereof.

I claim:

1. A surgical robotic system comprising:
   a robotic arm, an end effector movably connected to the robotic arm and provided with at least one movable end effector element driven by an actuator, and
   a force sensor arranged between the robotic arm and the end effector,
   wherein
   said actuator is formed by a hydraulic cylinder, and
   said robotic arm is provided with a hydraulic line connected to said hydraulic cylinder,
   wherein the cross-sectional area of the hydraulic cylinder is at least ten times the cross-sectional area of the hydraulic line.

2. The surgical robotic system according to claim 1, wherein the hydraulic cylinder is formed by a closed bellows.

3. The surgical robotic system according to claim 1, wherein the hydraulic line is operated by a hydraulic fluid, and wherein the hydraulic fluid is a saline solution.

4. The surgical robotic system according to claim 1, wherein the force sensor is formed as a force/moment sensor.

5. The surgical robotic system according to claim 1, wherein the hydraulic cylinder is arranged to symmetrically drive two of said movable end effector elements forming a gripping means.

6. The surgical robotic system according to claim 1, wherein the coupling of the hydraulic cylinder to the end effector element is formed in such a manner that an expansion of the hydraulic cylinder is to cause a closing movement of the end effector element.

* * * * *